United States Patent [19]

Pigneri

[11] Patent Number: 5,096,987
[45] Date of Patent: Mar. 17, 1992

[54] DIPROPARGYL ETHER OR ALPHA, ALPHA'-BIS(4-HYDROXYPHENYL)-PARA-DIISOPROPYLBENZENE

[75] Inventor: Anthony M. Pigneri, Houston, Tex.

[73] Assignee: Shell Oil Company, Houston, Tex.

[21] Appl. No.: 606,416

[22] Filed: Oct. 31, 1990

Related U.S. Application Data

[62] Division of Ser. No. 386,079, Jul. 28, 1989, Pat. No. 4,987,272.

[51] Int. Cl.$^5$ .............................. C08F 38/00
[52] U.S. Cl. .................... 526/172; 526/285
[58] Field of Search ................ 526/172, 285

[56] References Cited

U.S. PATENT DOCUMENTS

| | | | |
|---|---|---|---|
| 2,931,836 | 4/1960 | Cameron | 526/285 X |
| 3,051,693 | 8/1962 | Leto | 526/285 X |
| 3,300,456 | 1/1967 | Hay | 260/88.2 |
| 3,594,175 | 7/1971 | Hay | 96/115 |
| 3,694,412 | 9/1972 | Nozaki | 526/172 X |
| 4,226,800 | 10/1980 | Picklesmer | 260/465 |
| 4,946,928 | 8/1990 | Jackson | 528/205 |

FOREIGN PATENT DOCUMENTS

| | | |
|---|---|---|
| 293768 | 12/1988 | European Pat. Off. . |
| 899730 | 2/1962 | United Kingdom . |
| 1149697 | 4/1969 | United Kingdom . |
| 889782 | 9/1990 | World Int. Prop. O. . |

OTHER PUBLICATIONS

Hay, *Polymer Letters*, Part B, vol. 8, pp. 97-99 (1970).
Derlikov, Proceedings ACS Div. Polymeric Materials, 59, Fall 1988.

*Primary Examiner*—Joseph L. Schofer
*Assistant Examiner*—M. Nagumo

[57] ABSTRACT

Novel dipropargyl ether of alpha, alpha'-bis(4-hydroxyphenyl)-para-diisopropylbenzene is useful in preparing resins having desirable properties as laminates and the like.

12 Claims, No Drawings

DIPROPARGYL ETHER OR ALPHA, ALPHA'-BIS(4-HYDROXYPHENYL)-PARA-DIISOPROPYLBENZENE

This is a division of application Ser. No. 386,079 filed July 28, 1989, now U.S. Pat. No. 4,987,272.

BACKGROUND OF THE INVENTION

1. Field of the Invention

The present invention relates to the dipropargyl ether of alpha, alpha'-bis(4-hydroxyphenyl)-para-diisopropylbenzene and its use in resins, laminates and the like.

2. State of the Art

U.S. Pat. Nos. 4,226,800, 3,300,456, and 3,594,175; British patent 1,149,697; and Hay et al. *Polymer Letters*, Part B, Vol. 8, No. 2, 97–99 1970 describe various acetylene-terminated compounds, including the bispropargyl ether of bisphenol A. However, polymer resins prepared from this compound are undesirable for preparing electrical laminates because the resulting solutions thereof too readily run off reinforcing materials, such as fiberglass, and it is difficult to control the polymerization of the compound to provide a desired certain and reliable viscosity.

SUMMARY OF THE INVENTION

The present invention is directed to novel dipropargyl ether of alpha, alpha'-bis(4-hydroxyphenyl)-para-diisopropylbenzene of Formula I:

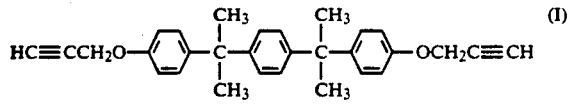

The compound, also known as dipropargyl ether of bishydroxycumylbenzene (DPE-BHCB), is useful in the preparation of polymers, including those having a high glass transition temperature (Tg) desirable in electrical laminates. The polymers also have a low dielectric constant, low moisture adsorption and more hydrocarbon in the polymer backbone. This result in the production of laminates with less run-off from the substrate and the laminates have a low dissipation factor useful in electrical applications.

The novel dipropargyl ether monomer of the invention can be prepared by known methods including reacting the corresponding di-hydric phenolic material, alpha, alpha'-bis(4-hydroxyphenyl)-para-diisopropylbenzene, with a propargyl halide, such as chloride or bromide, in an aqueous alkaline solution, such as aqueous sodium hydroxide solution as described in U.S. Pat. No. 4,226,800, the disclosures of which are incorporated by reference. One preferred method is by using propargyl chloride in an aqueous sodium hydroxide and a water-miscible, protic co-solvent, which is disclosed and claimed concurrently filed U.S. patent application Ser. No. 271,133, filed Nov. 14, 1988, now abandoned, the disclosures of which are incorporated by reference.

The novel dipropargyl ether monomer of the invention can be used to make various polymers and curable resins. The most common kind of polymer can be prepared by oxidative coupling according to known methods, including Hay et al., *Polymer Letters*, 8, pp. 97–99 (1970). Another kind of polymer can be prepared by thermal polymerization to give thermoset polymers that are crosslinked.

For electrical and electronic applications, a resin having a decomposition temperature higher than about 300° C. is desirable. By addition polymerization of the novel dipropargyl ether of Formula I of the invention, polymers are obtained which have (a) a sharp melting point and (b) dependable viscosity when used in solutions. For example, when preparing an electrical laminate on, e.g., fiberglass, using a solution of the dipropargyl ether of Formula I of the invention in a solvent, such as a blend of toluene, dimethyl formamide/acetone, the resulting polymer has a high, dependable viscosity after the solvent has been dried off and the polymer will coat the fiberglass much better with less run-off than the corresponding polymer of the dipropargyl ether of bisphenol A.

While not being limited to any theory, it is believed that the polymers have the Formula II

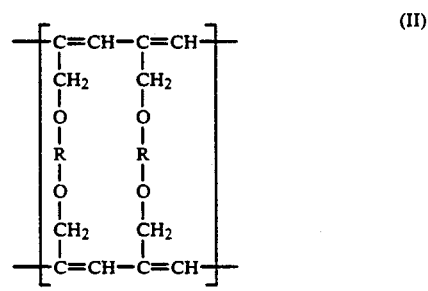

The catalysts which can be used in the present invention are conventional addition polymerization catalysts known in the art. Suitable catalysts include Group VI and Group VIII metal complex catalysts. Preferably, the addition polymerization catalyst is a nickel, platinum or palladium complex, such as molybdenum carbonyl, nickel acetylacetonate, tetrakis(triphenylphosphine)palladium O, bis(1,3-diphenyl(phosphino))ethane nickel II chloride, bis(triphenylphosphine)palladium II chloride and the like.

Another embodiment of the invention is directed to a method of preparing propargyl aromatic ether thermosetting polymers which comprises treating a propargyl aromatic ether with an effective amount of an addition polymerization catalyst.

Another embodiment of the invention is directed to a laminate comprising a thermosetting polymer of a propargyl aromatic ether prepared by polymerization of a propargyl aromatic ether in the presence of an effective amount of the polymerization catalyst and a fibrous filler or reinforcing material.

The curable composition of this invention can each be used in any desired form such as solid, solution or dispersion. These components are mixed in solvent or in the absence of a solvent to form the compositions of this invention. For example, the mixing procedure comprises mixing solutions of the composition in a suitable inert organic solvent or solvent blend, such as, for example, ketones such as acetone or methyl ethyl ketone, aprotic polar solvents, such as dimethyl formamide, aromatic hydrocarbons such as toluene, chlorinated hydrocarbons such as methylene chloride, ethers and the like, and homogenizing the resulting mixed solution at room temperature or at an elevated temperature below the boiling point of the solvents to form a composition in the form of a solution. When homogenizing these solutions at room temperature or at an elevated temperature, some reactions may take place between the constituent elements. So long as the resins components are maintained in the state of solution without gelation, such reactions do not particularly affect the operability of the resulting composition in, for example, a bonding, coating, laminating or molding operation.

The curable resin compositions of invention can be used in the above solution form as adhesives, paints vehicles, molding materials to be impregnated in substrates, or laminating materials. In this case, the concentration of the resin solid in the solution is determined so that the optimum operability can be obtained according to the desired utility.

The resin compositions of this invention can be used for various purposes in the form of dried powder, pellets, resin-impregnated product or compound. For example, compositions with the individual components uniformly mixed can be obtained by uniformly mixing the resin components in solution, and then removing the solvents from the homogeneous solution at reduced pressure or at an elevated temperature. Alternatively, solids components are kneaded at room temperature or at an elevated temperature to form a homogenized resin composition. The resin compositons can also melt blend and melt impregnate.

The curable composition of this invention may be reticulated by heating it alone to form a cured resin having heat resistance. In general, a catalyst may be used in order to promote crosslinking reaction of the components in the composition.

Examples of the catalysts include imidazoles, such as 2-methylimidazole, 2-undecylimidazole, 2-heptadecylimidazole, 2-phenylimidazole, 2-ethyl-4-methylimidazole, 1-benzyl-2-methylimidazole, 1-propyl-2-methylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, 1-guanaminoethyl-2-methylimidazole and addition product of an imidazole and trimellitic acid; tertiary amines, such as N,N-dimethyl benzylamine, N,N-dimethylaniline, N,N-dimethyltoluidine, N,N-dimethyl-p-anisidine, p-halogeno-N,N-dimethyl-aniline, 2-N-ethylanilino ethanol, tri-n-butylamine, pyridine, quinoline, N-methylmorpholine, triethanolamine, triethylenediamine, N,N,N',N'-tetramethylbutanediamine, N-methylpiperidine; phenols, such as phenol, cresol, xylenol, resorcinol, and phloroglucin; organic metal complexes or salts, such as copper tetrafluoroborate, lead naphthenate, lead stearate, zinc naphthenate, zinc octoate, tin oleate, dibutyl tin maleate, manganese naphthenate, cobalt naphthenate, and acetyl acetone nickel or iron, bis(triphenyl-phosphine)palladium II dichloride, tetrakis(triphenyl-phosphine)palladium O, bis(1,2-diphenylphosphino)e-thane nickel II chloride; and inorganic metal complexes and salts, such as stannic chloride, zinc chloride and aluminum chloride; peroxides, such as benzoyl peroxide, lauroyl peroxide, octanoyl peroxide, acetyl peroxide, para-chloro-benzoyl peroxide and di-t-butyl diperphthalate; acid anhydrides, such as maleic anhydride, phthalic anhydride, fumaric anhydride, pyromellitic anhydride, trimellitic anhydride, hexahydrophthalic anhydride, hexahydropyromellitic anhydride and hexahydrotrimellitic anhydride; azo compounds, such as azoisobutylonitrile, 2,2'-azobispropane, m,m'-azoxystyrene, hydrozones, and mixtures thereof. The amount of catalyst varies considerably according to the type of catalyst, the utility or curing conditions. They can, however, be used in catalytic amounts such as, for example, less than 5% by weight of the total composition. Bis(triphenylphosphine)palladium (II) dichloride is preferred.

A variety of additives may be added to the curable composition to impart specific properties provided that they do not impair the essential properties of the resulting resin. Examples of the additives include natural or synthetic resins, fibrous reinforcement, fillers, pigments, dyestuffs, thickening agents, wetting agents, lubricants, flame-retardants and the like.

The resin composition of this invention can also contain a white pigment such a titanium dioxide, a colored pigment such as yellow lead, carbon black, iron black, molybdenum red, prussian blue, ultramarine, cadmium yellow or cadmium red, and other various organic dyes and pigments in order to color the compositions. In addition to the above colored pigments, the resin compositions can also contain a rust-proofing pigment such as zinc chromate, red lead, red iron oxide, zinc flower or strotium chromate, an anti-sag agent such as aluminum stearate, a dispersing agent, a thickener, a coat modifier, a body pigment or a fire retardant, which are known additives for paints.

The compositions of this invention are cured by heating after applying it to a substrate as a coating or adhesive layer, or after molding or laminating in the form of powder, pellet or as impregnated in a substrate. The curing conditions of the curable composition of this invention depend on the proportion of components constituting the composition and the nature of the components employed. In general, the composition of this invention may be cured by heating it at temperature within the range of about 0°-300° C., preferably about 100° C.-250° C., although differing according to the presence of a catalyst or curing agent or its amount, or the types of the components in the composition. The time required for heating is generally 30 seconds to 10 hours, although considerably differing according to whether the resin composition is used as a thin coating or as molded articles of relatively large thickness or as laminates or as matrix resins for fiber reinforced composites, particularly for electrical and electronic applications, e.g., when applied to an electrically conductive material, such as copper, and susequently cured. Suitable fibrous reinforcing materials include glass fibers, quartz fibers, carbon fibers, boron fibers, Kevlar ® fibers, Teflon ® fibers and the like with woven or continouous glass fibers or carbon fibers being preferred. The fibrous or reinforcing material is present in the compositions of the invention in an amount effective to impart increased strength to the composition for the intended purpose, generally about 20 to about 95 w percent, usually about 35 to about 85 w percent, based on the weight of the total composition. When the resin composition of this invention is used for producing molded articles, laminated articles or bonded structures, the curing is desirably effected under pressure. Generally, this pressure is from 5 to 100 Kg/cm² (gauge).

The composition of this invention cures rapidly, even under mild conditions, so is especially suitable when quantity production and ease of workability are desired. The cured resin made from the composition not only has excellent adhesive force, bond strength, heat resistance, and electric properties, but also is excellent in mechanical properties and resistance to impact, chemicals, moisture and the like. The composition of this invention has a variety of uses as a coating material for rust prevention, flame resistance, flame retardance and the like; as electrical insulating varnish; as adhesive; in laminates to be used for furnitures, building materials, sheathing materials, electrical insulating materials, and the like; and in a variety of moldings.

ILLUSTRATIVE EMBODIMENTS

The present invention is further illustrated by the following embodiments which should not be regarded as limiting the invention in any way.

EMBODIMENT I

The dipropargyl ether of bishydroxycumylbenzene (BCHB) was prepared by treating 200 g of BCHB with 168 g of propargyl chloride added over about ½ hour at 135° F. in the presence of (a) sodium hyroxide in a molar ratio sodium hyroxide to phenol of 1.25 and (b) a reaction medium comprising 669 g of isopropyl alcohol (IPA) and 2050 g of water at 150°-155° F. The reaction was continued for about 25 hours while maintaining the pH ≧ 11. The reaction product was cooled to room temperature, where the product crystallized out of solution. This product was washed twice with IPA and then with water until a constant pH of wash water was obtained. The product crystals were then blown dry to obtain the desired product in 67% yield (179.8 g). Product was then recrystallized, by dissolving into boiling IPA, filtering to remove any residues and allowing to cool to room temperature. The filtrate, now cloudy and containing precipitate, was further cooled to 0° C. overnight. Then, the cold mixture was filtered, the solids washed with IPA, and dried in a vacuum oven overnight, at room temperature. A vacuum of 25 in Hg was maintained by bleeding nitrogen into the oven. Final realized yield was 58.7% W, or 157.4 grams.

EMBODIMENT 2

Prepregs were prepared from DPE-BHCB resin compositions as follows:

TABLE 1

Dipropargyl Ether Prepreg Manufacture from Solvent Borne Resin Varnish

| Property | Value |
| --- | --- |
| Resin | DPE-BHCB |
| Varnish Formulation, % w | |
| DPE-BHCB | 49.9 |
| Dimethyl formamide | 17.3 |
| Toluene | 16.4 |
| Acetone | 16.4 |
| Bis(triphenylphosphine)-palladiumdichloride, phr (ppm Pd) | .40(600) |
| Gel Time, Seconds @ 171° C. | 245 |
| Prepreg | |
| Glass Style | 7628 |
| Processing Conditions | 4.0 |
| Oven Time, Minutes | 4.0 |
| Oven Temperature, °C. | 163 |
| Resin Content, % w | 28 |

EMBODIMENT 3

Prepregs and laminates were prepared from DPE-BHCB resin compositions as follows:

TABLE 3

Dipropargyl Ether Prepreg and Laminate Preparation Using Resin Melt Coating Impregnation

| Property | Value |
| --- | --- |
| Resin | DPE-BHCB |
| Coating Mixture Formulation, % w | |
| DPE-BHCB | 100 |
| Bis(triphenylphosphine)-palladiumdichloride, ph (ppm Pd) | 0.40(600) |
| Gel Time, Seconds @ 171° C. | 340 |
| Prepreg | |
| Glass Style | 7628 |
| Processing Conditions | |
| Impregnation Time, Minutes | 2.5-3.0 |
| IMpregnation Temperature, °C. | 171 |
| Resin Content, % w | 41.3 |
| Lamination | |
| Laminate Construction | |
| Size, in × in. | 4 × 4 |
| Number of Plies | 8 |
| Actual Processing Conditions | 9 |
| Heat-up Rate, °F./Minute (avg.) | |
| Cure Schedule: | |
| Temperature, °F./Time, Hours | |
| Hold 1 (cure) | 600/1.5 |
| Hold 2 (postcure) | 400/1.7 |
| Hold 3 (postcure) | 440/1.5 |
| Hold 4 (postcure) | 480/0.5 |
| Pressure, psi | |
| During Heat-up, Start-End | 5-150 |
| During Cure | 150 |

The properties of the resulting laminates are set forth in Table 4 as compared to a standard brominated epoxy resin laminate.

TABLE 4

Dipropargyl Ether Laminate Properties

| Property | Value | |
| --- | --- | --- |
| Resin | DPE-BHCB | Brominated Epoxy |
| Laminate Resins Content | 34 | 40 |
| Dielectric Properties, @ 1 MHZ | | |
| Dielectric Constant | 3.62 | 4.55 |
| Dissipation Factor | 0.0033 | 0.015 |
| Thermal Properties | 175 | 140 |
| Glass Transiton Temperature, °C., DMA* Damping Peak | | |
| Coefficient of Thermal Expansion, ppm/°C., Average 50-250° C. | 124 | 220 |

*Dynamic Mechanical Analysis

As shown in Table 4 above, the dipropargyl ether resin laminates do have preferred lower dielectric constants and dissipation factors than the standard brominated epoxy resin laminate even at lower resin content. The Tg's of the dipropargyl ether-based laminates were also much higher than for the standard brominated epoxy resin-based laminate. The coefficient of thermal expansion of the dipropargyl ether-based laiminates are also lower than for the standard brominated epoxy-based laminate.

What is claimed is:

1. A process for preparing a curable polymeric composition which comprises contacting a monomer of structural formula:

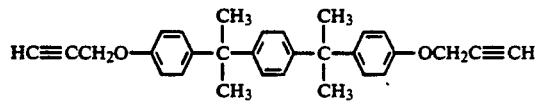

with an effective amount of an addition polymerization catalyst.

2. The process of claim 1 in which the addition catalyst is a Group VI or Group VIII metal complex.

3. The process of claim 1 in which the addition catalyst is a Group VIII metal complex.

4. The process of claim 2 in which the addition catalyst is a complex of nickel, palladium or platinum.

5. The process of claim 1 in which the addition catalyst comprises nickel acetylacetonate.

6. The process of claim 1 in which the addition catalyst comprises bis(triphenylphosphine)palladium II dichloride.

7. A composition comprising a dipropargyl ether of the structural formula

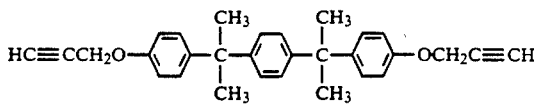

a Group VI or Group VIII metal complex addition polymerization catalyst, and a solvent.

8. The composition of claim 7 in which the polymerization catalyst is a Group VIII metal complex.

9. The composition of claim 8 in which the polymerization catalyst comprises a complex of nickel, palladium or platinum.

10. The composition of claim 7 in which the polymerization catalyst comprises nickel acetylacetonate.

11. The composition of claim 7 in which the polymerization catalyst comprises bis(triphenylphosphine)palladium II dichloride.

12. The composition of claim 7 in which the solvent comprises at least one of toluene, dimethyl formamide and acetone.

* * * * *